United States Patent
Maloney et al.

(10) Patent No.: US 9,486,396 B2
(45) Date of Patent: Nov. 8, 2016

(54) METAL SALT COMPOSITIONS

(75) Inventors: Venda Porter Maloney, Piscataway, NJ (US); Vyoma Patel, Parsippany, NJ (US); Steven Wade Fisher, Middlesex, NJ (US); Andre Michelle Morgan, Robbinsville, NJ (US); Michael Prencipe, Princeton, NJ (US); Stanislav Jaracz, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/996,036

(22) PCT Filed: Dec. 21, 2010

(86) PCT No.: PCT/US2010/061414
§ 371 (c)(1),
(2), (4) Date: Jun. 20, 2013

(87) PCT Pub. No.: WO2012/087288
PCT Pub. Date: Jun. 28, 2012

(65) Prior Publication Data
US 2013/0287709 A1 Oct. 31, 2013

(51) Int. Cl.
*A61K 8/58* (2006.01)
*A61K 8/27* (2006.01)
*A61Q 11/00* (2006.01)
*A61K 8/36* (2006.01)
*A61K 8/362* (2006.01)
*A61K 8/365* (2006.01)
*A61K 8/44* (2006.01)

(52) U.S. Cl.
CPC . *A61K 8/58* (2013.01); *A61K 8/27* (2013.01); *A61K 8/36* (2013.01); *A61K 8/361* (2013.01); *A61K 8/362* (2013.01); *A61K 8/365* (2013.01); *A61K 8/44* (2013.01); *A61Q 11/00* (2013.01)

(58) Field of Classification Search
USPC ......................................................... 424/49
See application file for complete search history.

(56) References Cited

U.S. PATENT DOCUMENTS

| | | | |
|---|---|---|---|
| 3,622,662 A | 11/1971 | Roberts et al. | |
| 3,624,199 A | 11/1971 | Norfleet et al. | |
| 4,022,880 A | 5/1977 | Vinson et al. | |
| 4,082,841 A | 4/1978 | Pader | |
| 4,100,269 A | 7/1978 | Pader | |
| 4,144,323 A | 3/1979 | Lamberti | |
| 4,154,815 A | 5/1979 | Pader | |
| 4,335,102 A | 6/1982 | Nakashima et al. | |
| 4,622,220 A * | 11/1986 | Frosch | 424/49 |
| 4,828,822 A | 5/1989 | Muhlemann et al. | |
| 4,839,157 A | 6/1989 | Mei-King Ng et al. | |
| 5,188,820 A * | 2/1993 | Cummins et al. | 424/49 |
| 5,240,697 A * | 8/1993 | Norfleet et al. | 424/52 |
| 5,603,922 A | 2/1997 | Winston et al. | |
| 5,695,746 A | 12/1997 | Garlick, Jr. et al. | |
| 5,776,435 A | 7/1998 | Gaffar et al. | |
| 5,858,333 A | 1/1999 | Winston et al. | |
| 6,036,944 A | 3/2000 | Winston et al. | |
| 6,169,118 B1 * | 1/2001 | Bilali | 424/463 |
| 6,929,790 B2 | 8/2005 | Kleinberg et al. | |
| 2008/0138298 A1 | 6/2008 | Glandorf et al. | |
| 2012/0045402 A1 * | 2/2012 | Morgan et al. | 424/52 |

FOREIGN PATENT DOCUMENTS

| | | |
|---|---|---|
| EP | 0026539 | 4/1981 |
| EP | 0425002 | 5/1991 |
| EP | 0426213 | 5/1991 |
| GB | 2167956 | 6/1986 |
| JP | S47-020351 | 9/1972 |
| JP | s48038864 | 11/1973 |
| JP | s48043871 | 12/1973 |
| JP | s56045407 | 10/1981 |
| JP | s56051409 | 12/1981 |
| JP | h03127719 | 5/1991 |
| JP | H05-000930 | 1/1993 |
| JP | H11-228368 | 8/1999 |
| JP | H11-246375 | 9/1999 |
| WO | WO 2007/076001 | 7/2007 |
| WO | WO 2008/042944 | 4/2008 |
| WO | WO 2010/138492 | 12/2012 |

OTHER PUBLICATIONS

International Search Report and Written Opinion in International Application No. PCT/US10/061414, mailed Nov. 9, 2012.
Corresponding Japanese Office Action dated Sep. 14, 2015.

* cited by examiner

*Primary Examiner* — Walter Webb

(57) ABSTRACT

Described herein are compositions comprising combinations of metal salts, and methods of preparing and using the same.

14 Claims, No Drawings

METAL SALT COMPOSITIONS

BACKGROUND

The amount of a given metal salt which can be incorporated into an oral care product is often limited as a result of unfavorable effects on the sensory experience of the user, for example, astringency, taste and mouth feel.

These limits on metal salt concentration have made it difficult to deliver an effective amount of a metal ion to the soft and/or hard tissue of the oral cavity using an oral care composition. Embodiments of the present invention provide compositions which address, inter alia, this problem.

SUMMARY

In some embodiments, the present invention provides an oral care composition comprising: a first metal salt, having a solubility of greater than 0.001 g/100 mL in water at 20° C.; a second metal salt having a solubility of 0.001 g/100 mL, or less, in water at 20° C.; and a free water content of greater than about 10%, by weight. In some embodiments, the first metal salt and second metal salt are independently selected from a zinc salt, a stannous salt and a copper salt. In some embodiments, the second metal salt is present in an amount effective to provide a synergistic increase in delivery of the metal ion of the first or second metal salt.

Some embodiments provide a method of treating or preventing a disease or condition of the oral cavity comprising contacting an oral cavity surface of a patient in need thereof with any one of the compositions described herein.

DETAILED DESCRIPTION

As used throughout, ranges are used as a short hand for describing each and every value that is within the range. Any value within the range can be selected as the terminus of the range.

In addition, all references cited herein are hereby incorporated by reference in their entireties.

In the event of a conflict in a definition in the present disclosure and that of a cited reference, the present disclosure controls.

As used herein, the term "soluble metal salt" refers to a metal salt having a solubility of greater than 0.001 g/100 mL in water at 20° C.

As used herein, the term "insoluble metal salt" refers to a metal salt having a solubility of 0.001 g/100 mL, or less, in water at 20° C.

In some embodiments, the present invention provides an oral care composition comprising: a first metal salt, having a solubility of greater than 0.001 g/100 mL in water at 20° C.; a second metal salt having a solubility of 0.001 g/100 mL, or less, in water at 20° C.; and a free water content of greater than about 10%, by weight. In some embodiments, the first metal salt and the second metal salt are independently selected from a zinc salt, a stannous salt and a copper salt.

In some embodiments, the second metal salt is present in an amount effective to provide a synergistic increase in delivery of the metal ion of the first or second metal salt. In some embodiments, the second metal salt is present in an amount effective to provide a synergistic increase in the uptake of the metal ion of the first or second metal salt. In some embodiments, the delivery or uptake is synergistically increased in oral cavity soft tissue. In some embodiments, the delivery or uptake is synergistically increased in an oral cavity hard surface, e.g. a tooth. Some embodiments provide compositions wherein the second metal is present in an amount effective to provide a synergistic increase in delivery or uptake of the metal ion of the first metal salt.

In some embodiments, the first metal salt and the second metal salt are salts of the same metal.

In some embodiments, the first metal salt is selected from: zinc citrate, zinc chloride, zinc lactate, zinc nitrate, zinc acetate, zinc gluconate, zinc glycinate and zinc sulfate. In some embodiments, the zinc citrate is in the form of zinc citrate trihydrate. In some embodiments, the first metal salt is zinc citrate trihydrate.

In some embodiments, the second metal salt is selected from: zinc oxide, zinc phosphate, zinc pyrophosphate, zinc silicate, zinc oleate, zinc hydroxide, zinc peroxide and zinc sulfide.

In some embodiments, the composition comprises from about 0.1 to about 5%, by weight, of the first metal salt; and from about 0.05 to about 2%, by weight, of the second metal salt. In some embodiments, the composition comprises from about 0.5 to about 4%, by weight, of the first metal salt; and from about 0.1 to about 1.5%, by weight, of the second metal salt. In other embodiments, the composition comprises from about 1 to about 3%, by weight, of the first metal salt; and from about 0.2 to about 0.75%, by weight, of the second metal salt.

Yet further embodiments provide compositions comprising: about 2%, by weight, of the first metal salt; and about 0.25%, by weight, of the second metal salt. While other embodiments provide compositions comprising: about 2%, by weight, of the first metal salt; and about 0.5%, by weight, of the second metal salt.

In some embodiments, the compositions further comprise one or more components selected from a fluoride ion source; a tartar control agent; a buffering agent; an antibacterial agent; an abrasive; and a combination of two or more thereof.

Some embodiments provide compositions wherein at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

Other optional additives may be included. Among such optional additives, included are those provided in order to change appearance or aesthetic appeal, and/or to preserve the final product, and/or for taste/cosmetic appeal and/or as therapeutic and prophylactic ingredients for oral health, prevention or treatment of a condition or disorder of hard or soft tissue of the oral cavity, or the prevention or treatment of a physiological disorder or condition.

Some embodiments provide a composition wherein a preservative is present. In some embodiments, the preservative is selected from parabens, potassium sorbate, benzyl alcohol, phenoxyethanol, polyaminopropryl biguanide, caprylic acid, sodium benzoate and cetylpyridinium chloride. In some embodiments, the preservative is present at a concentration of about 0.0001 to about 1%, by weight.

Colorants such as dyes may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-n-aphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sullophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cycl-ohexadienimine], FD&C Blue No. 1 (disodium salt of dibenzyldiethyl-diamino-triphenylcarbinol trisullonic acid anhydrite), FD&C Blue No. 2 (sodium salt of disulfonic acid of indigotin) and mixtures thereof in various proportions. Typically, colorants if included are present in very small quantities.

Flavoring agents include, but are not limited to, natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavoring agents can be used individually or in admixture. Commonly used flavors include mints such as peppermint, artificial vanilla, cinnamon derivatives, and various fruit flavors, whether employed individually or in admixture. Generally, any flavoring agent or food additive, such as those described in Chemicals Used in Food Processing, publication 1274 by the National Academy of Sciences, pages 63-258, may be used. Typically, flavoring agents, if included, are present at a concentration of from about 0.01 to about 1%, by weight. In some embodiments, the flavoring agent may be present at a concentration of about 0.2%, by weight.

Sweeteners include both natural and artificial sweeteners. Suitable sweeteners include water soluble sweetening agents such as monosaccharides, disaccharides and poysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame). In general, the effective amount of sweetener is utilized to provide the level of sweetness desired for a particular composition, will vary with the sweetener selected. This amount will normally be from about 0.001 to about 5%, by weight. In some embodiments, the sweetener is sodium saccharin and is present at a concentration of about 0.01%, by weight.

Whitening agents, material which is effective to effect whitening of a tooth surface to which it is applied, such as hydrogen peroxide and urea peroxide, high cleaning silica, preservatives, silicones, and chlorophyll compounds may be incorporated into the compositions of the present invention. In various embodiments, the compositions of this invention comprise a peroxide whitening agent, comprising a peroxide compound. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. One or more whitening agents are optionally present in a tooth-whitening effective total amount. In some embodiments the whitening agent is separated from the aqueous carrier. In some embodiments the whitening agent is separated from the aqueous carrier by encapsulation of the whitening agent.

Optionally, breath freshening agents may be provided. Any orally acceptable breath freshening agent can be used, including without limitation. One or more breath freshening agents are optionally present in a breath freshening effective total amount.

Other embodiments provide compositions wherein at least one of the one or more components is a tartar control agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J. In some embodiments, a phosphate is present at a concentration of from about 0.01 to about 10%, by weight. In some embodiments, a phosphate is present at a concentration of from about 1%, by weight.

Some embodiments provide compositions wherein a buffering agent is present. In some embodiments, sodium phosphate monobasic is present at a concentration of from about 0.01 to about 5%, by weight. In some embodiments, sodium phosphate monobasic phosphate is present at a concentration of about 1%, by weight. In some embodiments, sodium phosphate dibasic is present at a concentration of from about 0.01 to about 5%, by weight. In some embodiments, sodium phosphate dibasic phosphate is present at a concentration of about 0.15%, by weight.

Other optional additives include antimicrobial (e.g., antibacterial) agents. Any orally acceptable antimicrobial agent can be used, including Triclosan (5-chloro-2-(2,4-dichlorophenoxy)phenol); 8-hydroxyquinoline and salts thereof, zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride,); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; magnolia extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and clindamycin; and mixtures thereof. A further illustrative list of useful antibacterial agents is provided in U.S. Pat. No. 5,776,435, Gaffar, et al., issued Jul. 7, 1998. In some embodiments, the antimicrobial agent is present at a concentration of from about 0.001 to about 1%, by weight. In some embodiments, the antimicrobial agent is cetylpyridinium chloride. In some embodiments, cetylpyridinium chloride is present at a concentration of from about 0.001 to about 1%, by weight. In other embodiments, cetylpyridinium chloride is present at a concentration of about 0.05%, by weight.

Antioxidants are another class of optional additives. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Also optional, a saliva stimulating agent, useful for example in amelioration of dry mouth, may be included. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

Optionally, an antiplaque (e.g., plaque disrupting) agent may be included. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

Optional desensitizing agents include potassium citrate, potassium chloride, potassium tartrate, potassium bicarbonate, potassium oxalate, potassium nitrate, strontium salts, and mixtures thereof.

Optional additives also include vitamins, herbs and proteins. Vitamins include Vitamins C and D, thiamine, riboflavin, calcium pantothenate, niacin, folic acid, nicotinamide, pyridoxine, cyanocobalamin, para-aminobenzoic acid, bioflavonoids, pantheon, retinyl palmitate, tocopherol acetate, and mixtures thereof. Herbs such as *Chamomilla recutita, Mentha piperita, Salvia officinalis*, and *Commiphora myrrha* may optionally be included. Suitable proteins include milk proteins and enzymes such as peroxide-producing enzymes, amylase, plaque-disrupting agents such as papain, glucoamylase, glucose oxidase, and "next generation" enzymes."

In some embodiments, the composition has a free water content of greater than about 10%, by weight. In some embodiments, the composition has a free water content of greater than about 11%, by weight. In other embodiments, the composition has a free water content of greater than about 12%, by weight. Yet other embodiments provide compositions wherein the free water content is greater than about 13%, by weight. Still other embodiments provide compositions having a free water content of greater than about 14%, by weight. In some embodiments, the composition has a free water content of greater than about 15%, by weight. While other embodiments provide compositions have a free water content of greater than about 16%, by weight. In some embodiments, the composition has a free water content of about 17%, by weight. In some embodiments, the composition has a free water content of greater than about 17%, by weight. In some embodiments, the composition has a free water content of from about 10% to about 20%, by weight.

In some embodiments, the soluble metal salt and insoluble metal salt are not contained in a film. In some embodiments, the soluble metal salt and insoluble metal salt are in a single phase.

Some embodiments provide a method of treating or preventing a disease or condition of the oral cavity comprising contacting an oral cavity surface of a patient in need thereof with any one of the compositions described herein. In other embodiments, the disease or condition of the oral cavity is halitosis. In some embodiments, the present invention provides a method of reducing volatile sulfur compounds in the oral cavity of a subject in need thereof. In further embodiments, the present invention provides a method for increasing the delivery of a metal ion to an oral cavity surface.

In certain embodiments, the compositions described herein can be used, for example, for cavity prevention, whitening, plaque prevention or reduction, gingivitis prevention or reduction, tartar control, breath malodor prevention or reduction, and stain prevention.

The specific composition of the carrier preferably depends on the intended use of the composition. In various embodiments, the carrier is aqueous, comprising from about 5 to about 95%, by weight, water or from about 10 to about 70%, by weight, water. In other embodiments, the carrier is substantially non-aqueous. In a dentifrice carrier, water content can be from about 5 to about 70%, from about 10 to about 50%, or from about 20 to about 40%, by weight.

The carrier may comprise any of a variety of materials, including emulsifiers, thickeners, fillers, and preservatives. In some embodiments, the carrier may include a functional or active material, such as those described above.

In some embodiments, the carrier comprises a humectant, such as glycerin, sorbitol or an alkylene glycol such as polyethylene glycol or propylene glycol. In some embodiments, the carrier comprises a humectant at a level of from about 10 to about 80% by weight, or about 20 to about 60% by weight of the composition. Carrier compositions among those useful herein are disclosed in U.S. Pat. No. 5,695,746 to Garlick, Jr., et al. and U.S. Pat. No. 4,839,157 to Mei-King Ng et al.

Thickeners or gelling agents useful herein include inorganic, natural or synthetic thickeners or gelling agents. In some configurations, the carrier comprises the thickener and gelling agent at total levels of from about 0.1 to about 15% by weight, or from about 0.4 to about 10% by weight of the composition. Examples of thickeners and gelling agents useful herein include inorganic thickening silicas such as: an amorphous silica, for example Zeodent® 165 (Huber Corporation); Irish moss; iota-carrageenan; gum tragacanth; or polyvinylpyrrolidone.

In certain embodiments, the carrier comprises an abrasive or polishing agent, such as a silica, a calcined alumina, sodium bicarbonate, calcium carbonate, dicalcium phosphate or calcium pyrophosphate. In various embodiments, the carrier is clear. In various embodiments, the carrier comprises an abrasive at a level of from about 5 to about 70% by weight of the composition.

In some embodiments, the compositions comprise a surfactant or mixture of surfactants. Surfactants among those useful herein include water-soluble salts of at least one higher fatty acid monoglyceride monosulfate, such as the sodium salt of the monsulfated monoglyceride of hydrogenated coconut oil fatty acids; cocamidopropyl betaine; a higher alkyl sulfate such as sodium lauryl sulfate; an alkyl aryl sulfonate such as sodium dodecyl benzene sulfonate; a higher alkyl sulfoacetate; sodium lauryl sulfoacetate; a higher fatty acid ester of 1,2-dihydroxy propane sulfonate; and a substantially saturated higher aliphatic acyl amides of a lower aliphatic amino carboxylic acid, such as those having 12 to 16 carbons in the fatty acid, alkyl or acyl radicals; and mixtures thereof. Amides can be, for example, N-lauroyl sarcosine, and the sodium, potassium, and ethanolamine salts of N-lauroyl, N-myristoyl, or N-palmitoyl sarcosine. In various embodiments, the surfactant is present at a concentration of from about 0.3 to about 5% by weight of composition, or about 0.5 to about 3% by weight of composition.

Compositions as described herein can be prepared according to methods readily known to those skilled in the art.

Embodiments of the present invention are further described in the following examples. The examples are merely illustrative and do not in any way limit the scope of the invention as described and claimed.

EXAMPLES

Example 1

Table 1 (below) provides the formulation for exemplary compositions of the present invention.

TABLE 1

| Ingredient | % w/w |
| --- | --- |
| Gantrez (13% solution) | 11.5 |
| Glycerin | 11.5 |
| Zeodent 105 | 10 |
| Zeodent 114 | 10 |
| Polyethylene glycol | 3 |
| Tetrapotassium pyrophosphate | 2.4 |
| Zinc citrate trihydrate | 0.1-5 |
| Zeodent 165 | 1.8 |
| Sodium lauryl sulfate | 1.5 |
| Sodium hydroxide | 1.3 |

TABLE 1-continued

| Ingredient | % w/w |
| --- | --- |
| Flavor | 1.2 |
| Titanium dioxide | 1 |
| Sodium monofluorophosphate | 0.8 |
| Sodium CMC | 0.6 |
| Carrageenan | 0.4 |
| Sodium saccharin | 0.3 |
| Zinc oxide | 0.05-2 |
| Water | 17.6 |
| Sorbitol | q.s. |

Example 2

The delivery of zinc from exemplary compositions of the present invention to hydroxyapatite was compared to zinc delivery from compositions containing either a soluble or insoluble metal salt alone. The evaluation was performed using the following experimental procedure.

Compositions were diluted with water (1:2) to form a slurry. A saliva coated hydroxyapatite disk was added to the slurry. The disk remained in the slurry for about 10 minutes and was then rinsed three times with 5 mL of water. The disk was then digested with nitric acid and total zinc was measured by atomic absorption spectroscopy.

The data described in Table 2 (below) demonstrates that the addition of an insoluble metal salt (e.g. zinc oxide) to a composition comprising a soluble metal salt (e.g. zinc citrate) synergistically increases the delivery of the metal (zinc) to hydroxyapatite.

TABLE 2

| Formula | Zinc uptake (ug/disk) | Total Zinc (%) | Soluble Zinc (%) |
| --- | --- | --- | --- |
| 2% Zn Citrate | 33.7 ± 5.0 | 0.71 | 0.29 |
| 2% Zn Citrate + 0.25% ZnO | 69.0 ± 8.5 | 0.88 | 0.23 |
| 2% Zn Citrate + 0.5% ZnO | 135.9 ± 11.8 | 1.13 | 0.36 |
| 1.0% ZnO in silica base | 5.9 ± 0.4 | 0.60 | 0.07 |

Example 3

The uptake of zinc in the pig tongue and vitro skin was evaluated using the test procedures below.

Pig Tongue

Remove muscle portion of the tongue. Cut into 12 mm circles with cork borer. Glue circles to glass plates. Transfer into 24-well plate. Incubate with 1 mL of PBS buffer for 30 minutes at room temperature. Aspirate buffer, incubate for 2 minutes with 1 mL of 1:2 slurry of studied paste at 37° C. Aspirate slurry and rinse tissue 3× with 2 mL of deionized water. Transfer into a tube and digest with 1 mL of conc. nitric acid ($HNO_3$) overnight. Fill up to 15 mL with deionized water. Centrifuge for 30 minutes at 2500 RPM to obtain clear supernatant for submission for zinc analysis.

Vitro-Skin

Cut Vitro-skin (IMS Inc., Portland, Me.) into uniform circles of diameter between 10 to 14 mm. Cork borer could be used. The exact diameter will be necessary to calculate uptake per square centimeter. To remove the silicone coating, rinse the Vitro-skin circles (in bulk) 3 times with hexanes for 5 minutes. Air dry to evaporate hexanes. Soak Vitro-skin in sterilized and cleared saliva overnight in disposable polystyrene Falcon tube (mfc. code 352057). Use 1 mL of saliva per tissue. Perform in triplicate. Aspirate saliva, add 1 mL of 1:2 paste slurry and incubate for 2 minutes in 37° C. water bath. Operate quickly as uptake depends on exposure time at all temperatures. Aspirate the slurry and rinse 3-times with 5 mL of DI water for 10 seconds each. Use vortex for rinsing (max speed). Transfer the tissue into new polystyrene Falcon tube (mfc. code 352095). Process all samples at same speed. Add 1 mL of concentrated nitric acid to the tissue and incubate overnight. The tissue should dissolve completely. Add enough deionized water to fill it to 10 mL line. Shake well. Do not filter. Submit for zinc analysis. The obtained level of zinc (typically in ppm) must be multiplied by the total volume (10× in this case) to get μg of zinc per tissue ($U_T$). Table 3 (below) describes the data generated in the pig tongue and vitro-skin experiments described herein.

To calculate uptake of zinc per square centimeter, the following formula can be used:

$$U_R = 2 * U_T / (\pi * d^2) [\mu g/cm^2]$$

wherein:
$U_R$=(relative) zinc uptake per square centimeter of Vitro-skin (both sides)
$U_T$=zinc uptake per tissue
d=diameter of the tissue in centimeters

TABLE 3

| Formula | Zn uptake to pig tongue (μg/cm²) | Zn uptake to Vitro-skin (μg/cm²) | Soluble zinc (%) |
|---|---|---|---|
| 2% Zn Citrate | 13.5 ± 1.1 | 1.8 ± 0.5 | 0.24 |
| 2% Zn Citrate + 0.5% ZnO | 25.4 ± 7.4 | 12.0 ± 0.3 | 0.33 |
| 1% ZnO | not available | 2.2 ± 0.2 | 0.07 |
| 3% Zn Lactate | 21.2 ± 5.8 | 6.9 ± 1.0 | 0.52 |

Pig tongue is a suitable tissue representing a human tongue. Vitro-skin is a commercial product used as a standard for in-vitro skin related experiments.

The data described in Table 3 (above) demonstrates that metal salt uptake is synergistically increased by exemplary compositions of the present invention, which contain a combination of a soluble metal salt (e.g. zinc citrate) and an insoluble metal salt (e.g. zinc oxide).

As those skilled in the art will appreciate, numerous changes and modifications may be made to the embodiments described herein without departing from the spirit of the invention. It is intended that all such variations fall within the scope of the appended claims.

What is claimed is:

1. An oral care composition comprising:
   a first metal salt, having a solubility of greater than 0.001 g/100 mL in water at 20° C.;
   a second metal salt, having a solubility of 0.001 g/100 mL, or less, in water at 20° C.; and
   a free water content of greater than about 10%, by weight;
   wherein the first metal salt is zinc citrate and the second metal salt is zinc oxide;
   wherein the composition comprises from 0.1% to 5% by weight, of the first metal salt; and from 0.05% to 2% by weight, of the second metal salt;
   wherein the second metal salt is present in an amount effective to provide a synergistic increase in delivery of the metal ion of the first or second metal salt; and
   wherein the first metal salt and the second metal salt are in a single phase; and
   wherein the first metal salt and the second metal salt are not contained in a film.

2. The composition of claim 1, comprising: from 0.5 to 4%, by weight, of said first metal salt; and from 0.1 to 1.5%, by weight, of said second metal salt.

3. The composition of claim 1, comprising: from 1 to 3%, by weight, of said first metal salt; and from 0.2 to 0.75%, by weight, of said second metal salt.

4. The composition of claim 1, comprising: about 2%, by weight, of said first metal salt; and about 0.25%, by weight, of said second metal salt.

5. The composition of claim 1, comprising: about 2%, by weight, of said first metal salt; and about 0.5%, by weight, of said second metal salt.

6. The composition of claim 1, further comprising one or more components selected from a fluoride ion source; a tartar control agent; a buffering agent; an antibacterial agent; an abrasive; and a combination of two or more thereof.

7. The composition of claim 6, wherein at least one of the one or more components is a fluoride ion source selected from: stannous fluoride, sodium fluoride, potassium fluoride, sodium monofluorophosphate, sodium fluoro silicate, ammonium fluorosilicate, amine fluoride, ammonium fluoride, and a combination of two or more thereof.

8. The composition of claim 6, wherein at least one of the one or more components is a tartar control agent selected from: sodium tripolyphosphate, sodium tetrapolyphosphate, mono, di, tri- and tetrasodium pyrophosphates, sodium trimetaphosphate, sodium hexametaphosphate; potassium tripolyphosphate, potassium tetrapolyphosphate, mono, di, tri- and tetrapotassium pyrophosphates, potassium trimetaphosphate, potassium hexametaphosphate; and a combination of two or more thereof.

9. The composition of claim 1, wherein the composition comprises greater than about 15%, by weight, free water.

10. A method of treating a disease or condition of the oral cavity comprising contacting an oral cavity surface of a patient in need thereof with the composition of claim 1.

11. The method of claim 10, wherein the disease or condition of the oral cavity is halitosis.

12. The composition of claim 1, wherein the composition comprises greater than about 15%, by weight, free water.

13. The composition of claim 12, comprising: from 1 to 3%, by weight, of said first metal salt; and from 0.2 to 0.75%, by weight, of said second metal salt.

14. The composition of claim 13, further comprising one or more components selected from a fluoride ion source; a tartar control agent; a buffering agent; an antibacterial agent; an abrasive; and a combination of two or more thereof.

* * * * *